(12) United States Patent
Santala et al.

(10) Patent No.: US 12,396,658 B2
(45) Date of Patent: *Aug. 26, 2025

(54) SYSTEM AND METHOD FOR APNEA DETECTION (71) Applicant: GE Precision Healthcare LLC, Waukesha, WI (US)

(72) Inventors: Robert Filip Arnold Santala, Helsinki (FI); Panu Takala, Helsinki (FI); Juha Virtanen, Helsinki (FI)

(73) Assignee: GE Precision Healthcare LLC, Waukesha, WI (US)

( * ) Notice: Subject to any disclaimer, the term of this patent is extended or adjusted under 35 U.S.C. 154(b) by 166 days.

This patent is subject to a terminal disclaimer.

(21) Appl. No.: 18/467,052

(22) Filed: Sep. 14, 2023

(65) Prior Publication Data

US 2023/0414128 A1 Dec. 28, 2023

Related U.S. Application Data

(63) Continuation of application No. 16/007,434, filed on Jun. 13, 2018, now Pat. No. 11,806,127.

(51) Int. Cl.
*A61B 5/08* (2006.01)
*A61B 5/00* (2006.01)
*A61B 5/0535* (2021.01)
*A61B 5/085* (2006.01)

(52) U.S. Cl.
CPC .......... *A61B 5/0826* (2013.01); *A61B 5/0535* (2013.01); *A61B 5/086* (2025.01); *A61B 5/6823* (2013.01); *A61B 5/7278* (2013.01); *A61B 5/7282* (2013.01); *A61B 2562/0209* (2013.01)

(58) Field of Classification Search
CPC ..... A61B 5/0826; A61B 5/0535; A61B 5/086; A61B 5/6823; A61B 5/7278; A61B 5/7282; A61B 2562/0209
See application file for complete search history.

*Primary Examiner* — Jacqueline Cheng
*Assistant Examiner* — Tho Q Tran (57) ABSTRACT

An impedance-based respiration monitoring system for apnea detection includes at least three surface electrodes configured to record impedance respiration data from a patient's torso, a signal processing system, and an apnea detection module. The signal processing system is configured to generate a first respiration lead formed by a first set of surface electrodes from the at least three surface electrodes, the first respiration lead providing a first series of impedance measurements, and to generate a second respiration lead formed by a second set of surface electrodes attached to the patient's torso, the second lead providing a second series of impedance measurements. The apnea detection module is executable on a processor to calculate a first apnea metric based on the first series of impedance measurements, and calculate a second apnea metric based on the second series of impedance measurements. An apnea event is then detected based on the first apnea metric and the second apnea metric.

9 Claims, 9 Drawing Sheets

SYSTEM AND METHOD FOR APNEA DETECTION

CROSS-REFERENCE TO RELATED APPLICATION

The present application is a continuation of U.S. patent application Ser. No. 16/007,434, filed on Jun. 13, 2018 at the United States Patent and Trademark Office. The entire contents of the above-referenced application are hereby incorporated by reference for all purposes.

BACKGROUND

The present disclosure relates to apnea detection methods and systems, and more particularly to impedance-based respiration monitoring systems for reliable apnea detection, and corresponding methods.

Impedance-based respiration monitoring is a common technique for measuring respiration, which measures the impedance between two electrodes to monitor a patient's breathing activity. Typically, the impedance-based respiration monitors employ two electrodes on the patient's thorax, which are typically the right arm and left leg electrodes. Traditionally, this measurement is done as an additional measurement to electrocardiogram (ECG) monitoring, and thus uses a subset of the ECG electrodes to conduct the respiration monitoring. In such embodiments, one signal vector (or lead) of respiration is monitored using one of the ECG leads.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an impedance-based respiration monitoring system for apnea detection includes at least three surface electrodes configured to record impedance respiration data from a patient's torso, a signal processing system, and an apnea detection module. The signal processing system is configured to generate a first respiration lead formed by a first set of surface electrodes from the at least three surface electrodes, the first respiration lead providing a first series of impedance measurements, and to generate a second respiration lead formed by a second set of surface electrodes attached to the patient's torso, the second lead providing a second series of impedance measurements. The apnea detection module is executable on a processor to calculate a first apnea metric based on the first series of impedance measurements, and calculate a second apnea metric based on the second series of impedance measurements. An apnea event is then detected based on the first apnea metric and the second apnea metric.

In one embodiment, a method of impedance-based apnea metric monitoring for apnea detection includes receiving a first series of impedance measurements from a first respiration lead formed by a first set of surface electrodes attached to a patient's torso, and receiving a second series of impedance measurements from a second respiration lead formed by a second set of surface electrodes attached to the patient's torso. A first apnea metric is calculated based on the first series of impedance measurements, and a second apnea metric is calculated based on the second series of impedance measurements. An apnea event is then detected based on the first apnea metric and the second apnea metric.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Through their experimentation and research in the relevant field, the present inventors have recognized that presently available respiration monitoring systems for apnea detection are integrated into ECG systems and considered a secondary physiological parameter that is subordinate to the ECG measurement. Thus, electrode arrangements and measurement techniques are optimized for ECG measurement, rather than apnea monitoring and detection. Accordingly, current apnea metric monitors do not provide reliable measurement of apnea metrics and apnea detection. Current ECG/respiration measurement systems are not viable as apnea detection devices because they are prone to false alarms.

Accordingly, the present inventors have recognized a need for a dedicated impedance-based apnea monitor specifically adapted for apnea detection, where the electrode locations and control logic are optimized for respiration measurement. Namely, the electrode placements can be optimized for obtaining the most reliable impedance measurement, rather than for recording cardiac waveforms. The inventors conducted several studies for the purpose of identifying optimal electrode placements and lead arrangements, as well as to develop various measurement techniques. Through their experimentation and research, the inventors have recognized that certain electrode pairs, or leads, yield the largest signal amplitude for most patients.

Likewise, the inventors have endeavored to determine which electrode arrangements and measurement techniques yield the most reliable apnea metric, and thus apnea detection, information. Through their experimentation and research, the inventors recognized that single lead arrangements do not capture all types of patient breathing patterns. Namely, the inventors recognized that at least two leads are required for conducting reliable respiration and apnea metric monitoring, where one lead is optimized for measuring thoracic breathing activity and the second lead is optimized for measuring abdominal breathing activity. Thoracic breathing activity, which is considered to be the most common method of breathing for awake adults, involves using the intercostal muscles to elevate the lungs to begin respiration. Abdominal breathing occurs when the diaphragm muscles control the respiratory cycle. Abdominal breathing is considered the most efficient breathing mode, as it involves a larger breath volume and encourages more air to enter the lower lobes of the lung where there is a higher concentration of blood vessels. Abdominal breathing is the mode of respiration utilized by infants and, typically, in relaxed, sleeping, or otherwise unconscious adults.

Through their experimentation and research, the inventors have recognized that current, single lead respiration monitors are unable to capture both thoracic and abdominal breathing. Generally, patients tend to either emphasize the movement of the upper thorax area, thoracic breathing, or the abdomen area, abdominal breathing. Different patients may emphasize one breathing motion or the other, and individual patients may also switch between the two breathing mechanisms. The single lead, which in current systems is typically on the thorax, is unable to capture both breathing mechanisms. Accordingly, current systems produce a significant number of false alarms because healthy breathing activity, such as abdominal breathing activity, goes undetected. The inventors have recognized that, by individually monitoring both the thoracic area and the abdominal area by separate leads, complementary information can be provided about the apnea metric and the respiration activity can be sufficiently captured in order to avoid false apnea alarms.

Figure 1:
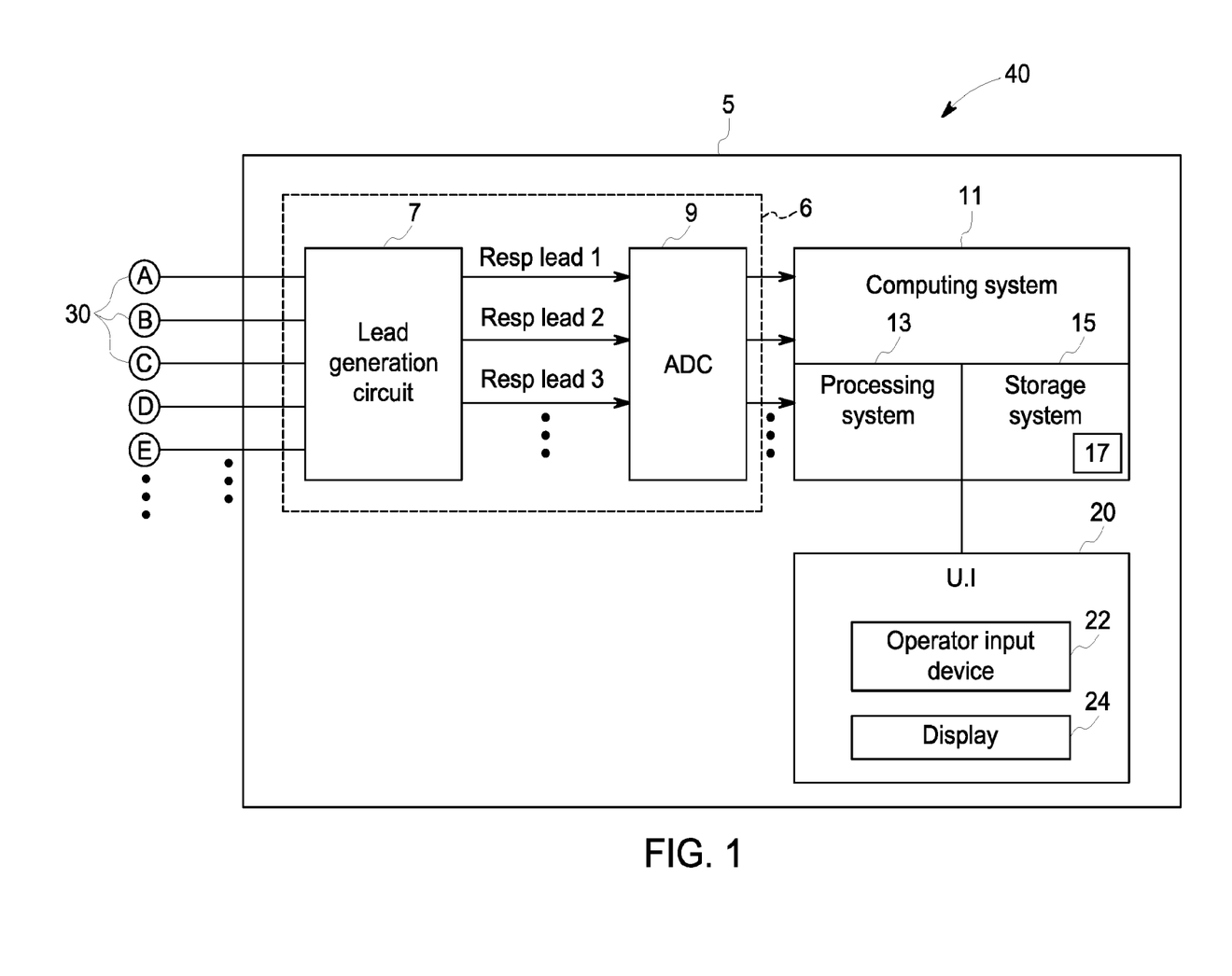
FIG. 1 is a schematic diagram of an exemplary impedance-based respiration monitoring system according to the present disclosure.

FIG. 1 depicts an exemplary impedance-based respiration monitoring system 40 for apnea detection. The system provides two or more continuous respiration leads with complementary data for providing a more reliable calculation of the apnea metric and minimizing false apnea alarms. The system provides additional valuable information derived from the independence respiration measurements provided by each lead. For example, the thoracic breathing activity can be compared to the abdominal breathing activity, and patterns may be detected in one or both activities that may allow early apnea, or pre-apnea, detection. For example, changes in the breathing pattern between the thoracic area and the abdominal area may indicate an upcoming apnea event. Other respiratory dysfunctions may be detected similarly based on recognizable patterns in the activity of the two different leads.

FIGS. 2A-2C, 3A-3D, and 4 exemplify electrode arrangements that may be utilized to generate two or more leads of respiration data, including at least one respiration lead measuring thoracic breath activity and at least a second respiration lead measuring abdominal breath activity. In the depicted embodiments, the first respiration lead 1 is configured to measure thoracic breath activity and the second respiration lead 2 is configured to measure abdominal breath activity. The exemplary system 40 in FIG. 1 includes five electrodes 30, including electrodes A-E, connected to and providing impedance measurements to a respiration monitor 5. As depicted in the various examples shown and described herein, any number of three or more electrodes 30 may be utilized for generation of two or more respiration leads, including at least a first respiration lead 1 and a second respiration lead 2. Any number of respiration leads may be derived from the electrodes 30, e.g., electrodes A-E, attached to the patient 41. In certain embodiments, a third respiration lead 3 may be provided, and in other examples and additional a fourth respiration lead 4 may also be provided.

Each of the three or more electrodes 30 includes an electrode portion that adheres to the patient and receives carrier frequencies injected from another electrode for the purpose of impedance measurement. Each electrode 30 further includes electrical wires that connect to the respiration monitor 5. The respiration monitor 5 includes a signal processing system 6 that generates at least two respiration leads, including a first respiration lead 1 representing the patient's thoracic breath activity and a second respiration lead 2 representing the patient's abdominal breath activity. In the depicted embodiment, the signal processing system 6 includes a lead generation circuit 7 and an analog-to-digital converter (ADC) 9. The lead generation circuit 7 is configured to amplify the input signals from the respective electrodes 30 and compare pairs thereof to generate respiratory lead signals. In the depicted embodiment, the lead generation circuit 7 is an analog signal processing circuit configured to compare pre-set input pairs to generate respective analog respiratory lead signals. Those analog respiratory lead signals are then digitized in a multi-channel ADC 9. However, in other embodiments, the input signals from the electrodes 30 may be digitized at an initial signal processing stage, and the lead generation may be digitally performed. Various analog and digital signal processing systems for lead generation are well known in the relevant art, and a person having ordinary skill in the art will understand in light of the present disclosure how to implement any of various signal processing systems to generate digital respiratory lead signals using the disclosed inputs and measurement methods.

The respiration monitor 5 further includes a computing system 11 comprising at least a processing system 13 and a storage system 15. An apnea detection module 17 is stored within the storage system 15 and executable by the processing system 13 to facilitate calculation of an apnea metric for each respiration lead (e.g. 1-4) and detect an apnea event based thereon. In certain embodiments, the apnea detection module 17 may comprise instructions partly or entirely housed and executed remotely from the respiration monitor 5, such as on the computing system of the computer network of a healthcare facility. In such embodiments, respiration lead data may be transmitted wirelessly over the wireless network of a healthcare facility and processed by a network computing system.

The processing system 13 may be implemented with a single processing device, but may also be distributed across multiple processing devices or subsystems that cooperate in executing program instructions. The processing system 13 includes one or more processors, which may each be a microprocessor, a general purpose central processing unit, an application-specific processor, a microcontroller, or any other type of logic-based device. The processing system 13 may also include circuitry that retrieves and executes software, including the apnea detection module, from the respective storage system 15.

The storage system 15 can comprise any storage media, or group of storage media, readable by the respective processing system 13 and capable of storing software. The storage system 15 may include volatile and non-volatile, removable and non-removable media implemented in any method or technology for storing information, such as computer-readable instructions, program modules comprising such instructions, data structures, etc. The storage system 15 may be implemented as a single storage device, but may also be implemented across multiple storage devices or subsystems. Examples of storage media include random access memory, read only memory, optical discs, flash memory, virtual memory, and non-virtual memory, or any other medium which can be used to store the desired information and that may be accessed by an instruction execution system, as well as any combination of variation thereof. The storage media may be housed locally with the processing system 13 or may be distributed, such as distributed on one or more network servers, such as in cloud computing applications and systems. In some implementations, the storage media is non-transitory storage media. In some implementations, at least a portion of the storage media may be transitory.

The respiration monitor 5 further includes a user interface 20 by which an operator can provide control inputs through the operator input device 22 and view visual outputs on the display 24. For example, the computing system 11 may be configured to control the display 24 to provide information regarding the apnea metrics calculated for the patient and/or to provide a visual indicator of an apnea alert alerting a clinician or operator of an apnea event. Furthermore, the display may be configured to display control options and/or to display control settings for view by the operator. The operator input device 22 may include any known user input device appropriate for a patient monitoring application, such as a keypad, one or more control knobs or dials, etc. In certain embodiments the operator input device 22 may be a touch screen, and thus may be incorporated in and provided as part of the display 24.

Figure 2A:
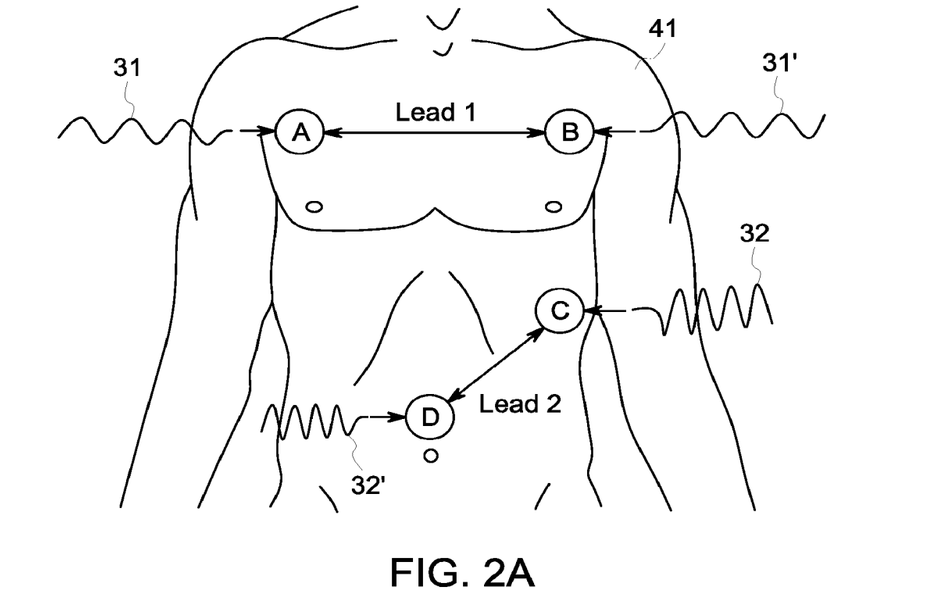
FIGS. 2A-2C depict exemplary lead arrangements employing four receiving electrodes, and accompanying measurement methods.
Figure 2B:
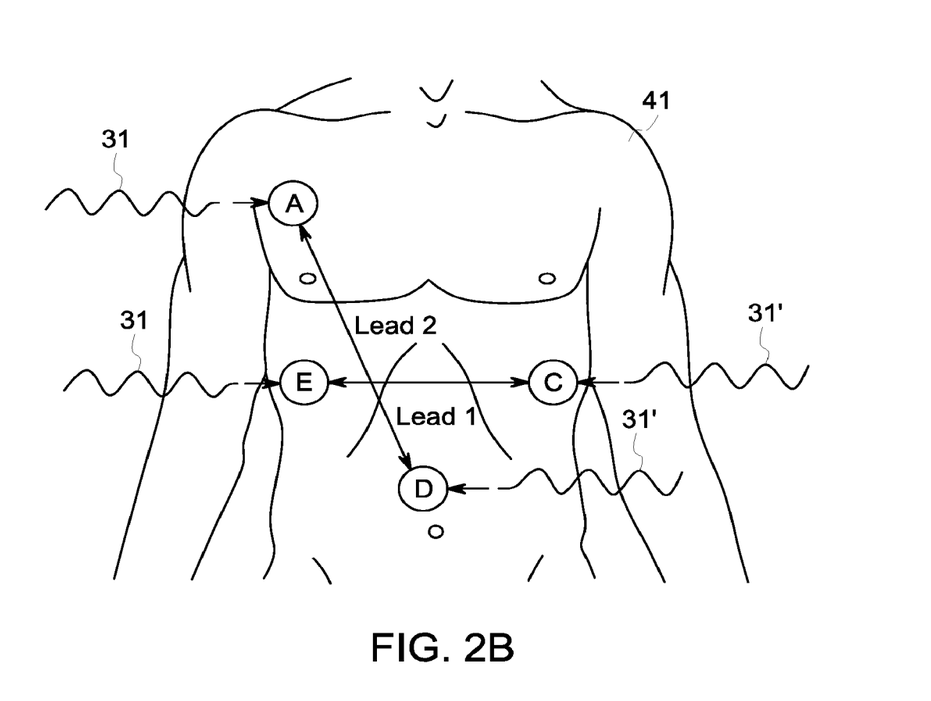
Figure 2C:
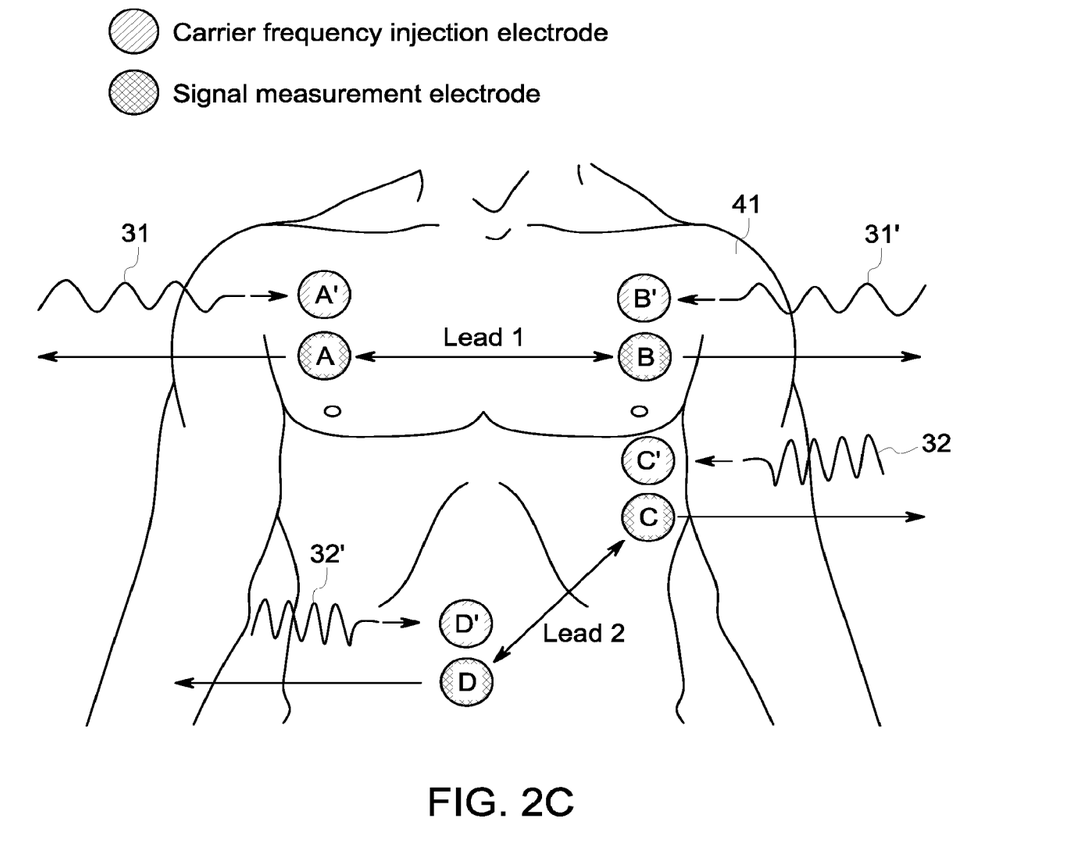

Through their experimentation and research, the inventors developed certain lead configurations which are especially effective at capturing the full range of patient respiration activity. In the depicted embodiments, the first respiration lead 1 is configured to measure thoracic breath activity and the second respiration lead 2 is configured to measure abdominal breath activity. Exemplary lead configurations are provided in FIGS. 2-5. FIGS. 2A-2C illustrate a two lead configuration where each lead is comprised of a separate set of two recording electrodes. FIGS. 3A-3D depict two lead configurations formed by three electrodes, where one recording electrode is shared by both leads. FIG. 4 depicts a four lead configuration, where two leads (respiration lead 1 and respiration lead 3) measure thoracic breath activity, and two leads (respiration lead 2 and respiration lead 4) measure abdominal breath activity.

In FIG. 2A, four electrodes 30 are provided, including electrodes A-D. Electrodes A and B are positioned on the upper thorax, and thus the impedance measurements in the first respiration lead between electrodes A and B capture the thoracic breath activity. The second respiration lead 2 provides the impedance measurements between electrode C and electrode D. Electrode C is positioned on the lower thorax, and specifically on the patient's left lower thorax. Electrode D is positioned in the center of the patient's abdomen. The impedance measurements provided between electrode C and electrode D capture the patient's abdominal breath activity.

There are generally two different mechanisms contributing to the signal generation in impedance respiration measurement. The first contribution, which is the classical explanation for impedance-based respiration measurements, is that the air volume in the lungs modulates the impedance measured through the volume conductor. In other words, the greater the volume of the air in the lungs, the greater the impedance across the lungs. The second contribution is that the impedance signal is generated from deformation of issue underneath and adjacent to the receiving electrode 30. This second contribution is actually believed to provide the majority of the impedance respiration signal. However, both mechanisms do contribute to the measured impedance change throughout the respiration cycle, and thus impedance respiration signal. Furthermore, the contributions of the two mechanisms may depend on the chosen measurement signal and electrode locations.

FIGS. 2A-2B and 3A-3C exemplify various two-electrode measurement configurations where a carrier signal is injected and recorded by the set of two electrodes. FIGS. 2C and 3D depict an electrode arrangement in which separate drive and sense electrodes are used, and thus each lead is generated by a four-electrode measurement arrangement. In the case of the two-electrode measurement technique, the measurements are more influenced by the second contributing mechanism of the tissue deformation because the two-electrode arrangement has a higher transmission dependency, and thus sensitivity to the tissue underneath the electrodes. The four-electrode measurement arrangement, which has separate drive and sense electrodes, is less sensitive to the tissue underneath the electrodes, and thus the change in air volume in the lungs during the breath activity provides a more significant contribution to the change in impedance than it does for the two-electrode arrangement.

The inventors developed various ways for providing lead differentiation to enable each of the two or more leads of breath activity data to be measured within the same time period. Namely, in order to retrieve both thoracic breath activity and abdominal breath activity in two separate measurements throughout each breath, the respiration leads must be separated from each other. This can be done either in the frequency domain or in the time domain. For frequency domain separation, different excitation frequencies, or carrier frequencies, may be used for conducting the impendence measurements in the respective leads. Alternatively, phase shifting may be used, where the same signal is provided at two different phases so that the signals in each of the leads can be differentiated. Additionally, in a time multiplexed shared electrode configuration, phase shifting can be used to balance the contribution of the electrodes. By phase shifting, the sum current in the shared electrode can be normalized to the current of the other individual electrodes. In either such frequency domain embodiment, the measurements in each of the leads can be conducted independently and simultaneously. If time domain separation is used, on the other hand, time division multiplexing must be utilized to coordinate the measurements in each of the leads. Thus, the transmission and receipt of the signals in each of the leads are coordinated and alternated, which can be done at a rate such that sufficient measurement samples can be made in each of the leads to provide a through representation of the breath activity at each location.

The measurement may be conducted in each lead by using dual-ended sampling methods or single-ended sampling methods. FIGS. 2A and 2B represent exemplary embodiments where dual ended sampling methods are used employing two different carrier frequencies for separating the leads. Referring to FIG. 1, for the first respiration lead 1 a first carrier frequency at a first phase 31 is injected at electrode A and is received, or sensed, at electrode B. That same frequency at a second phase 31' is injected at electrode B and is received at electrode A. For example, the signal injected at electrode B may be an opposite phase, 180 degree phase shift, from that injected in electrode A. Accordingly, the impedance measurements provided at the respiration lead 1 are robust two-way impedance measurements. The same two-way measurement technique can be utilized at electrodes C and D to form the second respiration lead 2. However, a different frequency (32, 32') is used for lead 2 than for lead 1. Thereby, the information specific to the respective electrode pair can be separated based on the carrier frequencies.

Any two carrier frequencies may be utilized, so long as they can be separated by demodulation. In certain embodiments, very different frequencies may be utilized. To provide just one example, the carrier frequencies for the different leads may be 1 kHz and 50 kHz, which are very easily separated. However, in other embodiments the carrier frequencies may be much closer together. For example, in certain embodiments where appropriate signal processing systems are provided, the carrier frequencies may be within 1% of one another, such as carrier frequencies of 50 kHz and 50.5 kHz.

FIG. 2C exemplifies the same lead arrangement as depicted in FIG. 2A, except using the single-ended sampling arrangement. The single-ended sampling employs the four-electrode arrangement described above, where each lead is formed by four separate electrodes attached to the patient. In the example of FIG. 2C, a first carrier frequency at a first phase 31 is injected by injection electrode A' and is received by both electrode A and electrode B. The first frequency at a second phase 31' is injected by injection electrode B', and is also received at both electrodes A and B, which are dedicated measurement electrodes. Similarly, injection electrodes C' and D' inject a second frequency at two different phases 32, 32', which are then received at the dedicated signal measurement electrodes C and D to form respiration lead 2.

As an alternative to utilizing two different frequencies, both the single-ended and dual-ended sampling arrangement can be conducted using time division multiplexing to separate the leads. FIG. 2B depicts the time division multiplexing arrangement utilizing a single frequency and a dual-ended sampling arrangement. Namely, for the depicted electrode configuration, the first frequency is injected at opposite phases 31, 31' into electrodes C and E, and is also sampled at each electrode, to provide a first impedance measurement in the first respiration lead 1 representing the thoracic breath activity. The first frequency is then injected at opposite phases 31, 31' into electrodes A and D and simultaneously received therefrom, to generate an impedance measurement for the second respiration lead 2. The system alternates between measurement at lead 1 and lead 2 throughout a particular breath cycle to generate the first series of impedance measurements and the second series of impedance measurements.

Figure 3A:
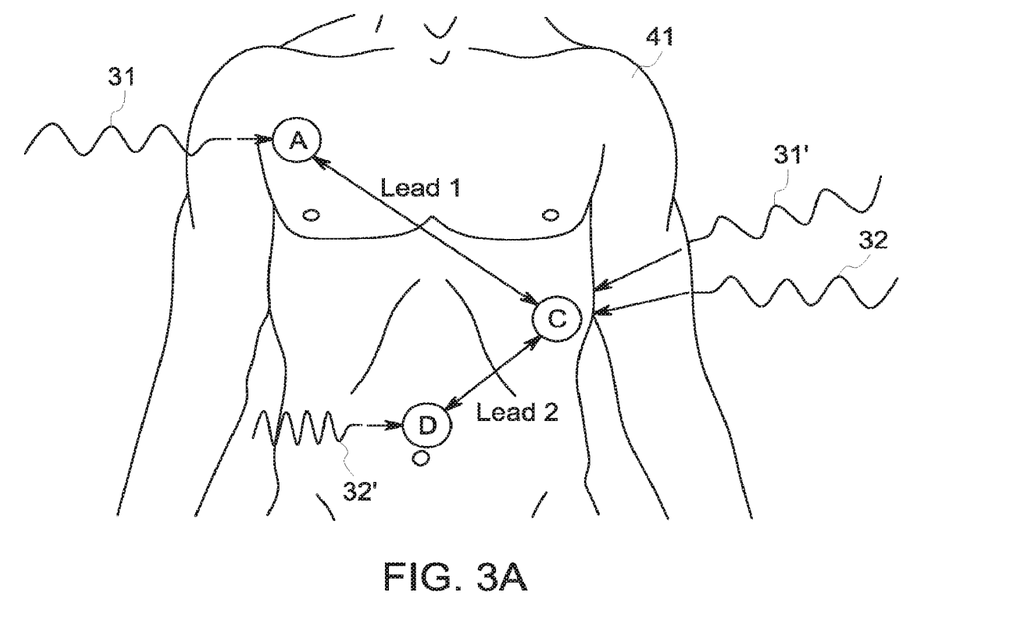
FIGS. 3A-3D depict exemplary lead arrangements employing three receiving electrodes, and accompanying measurement methods.
Figure 3B:
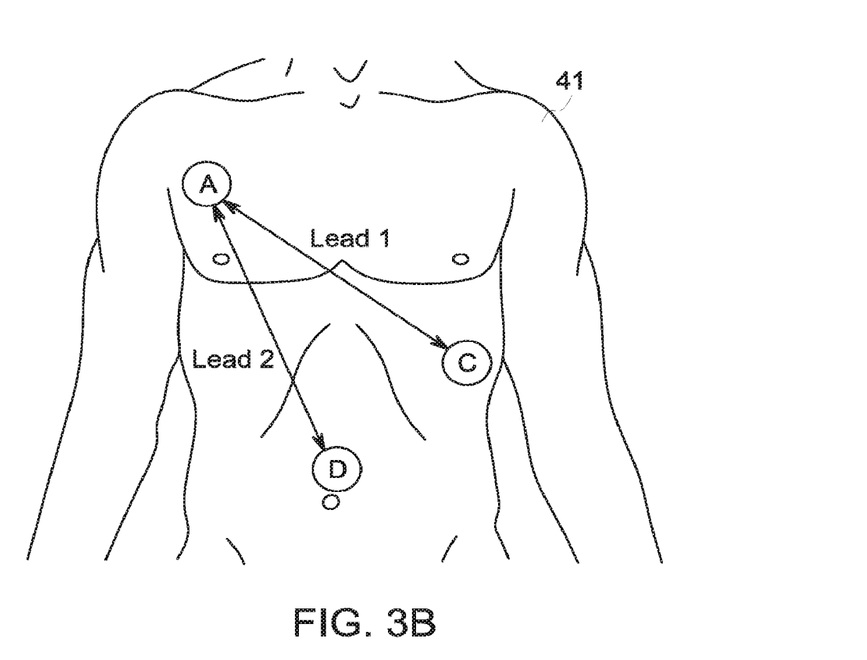
Figure 3C:
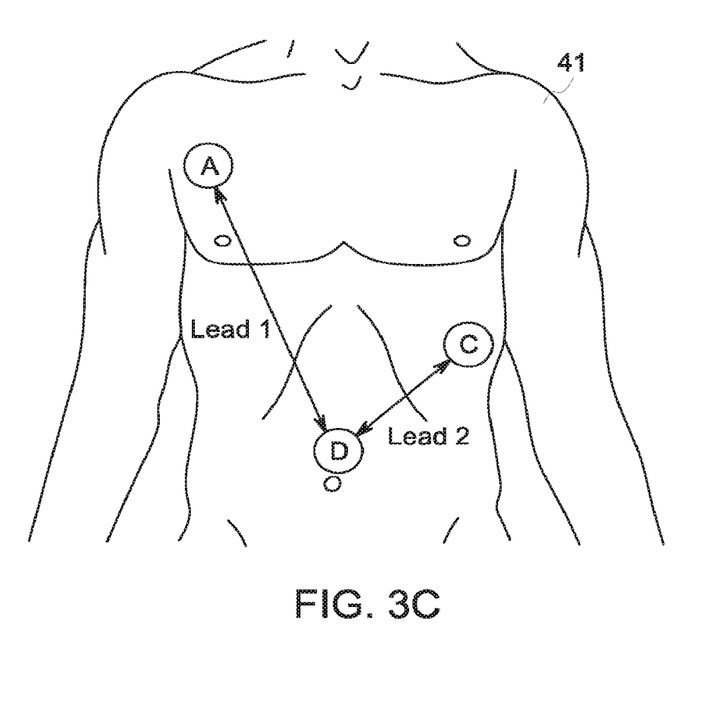
Figure 3D:
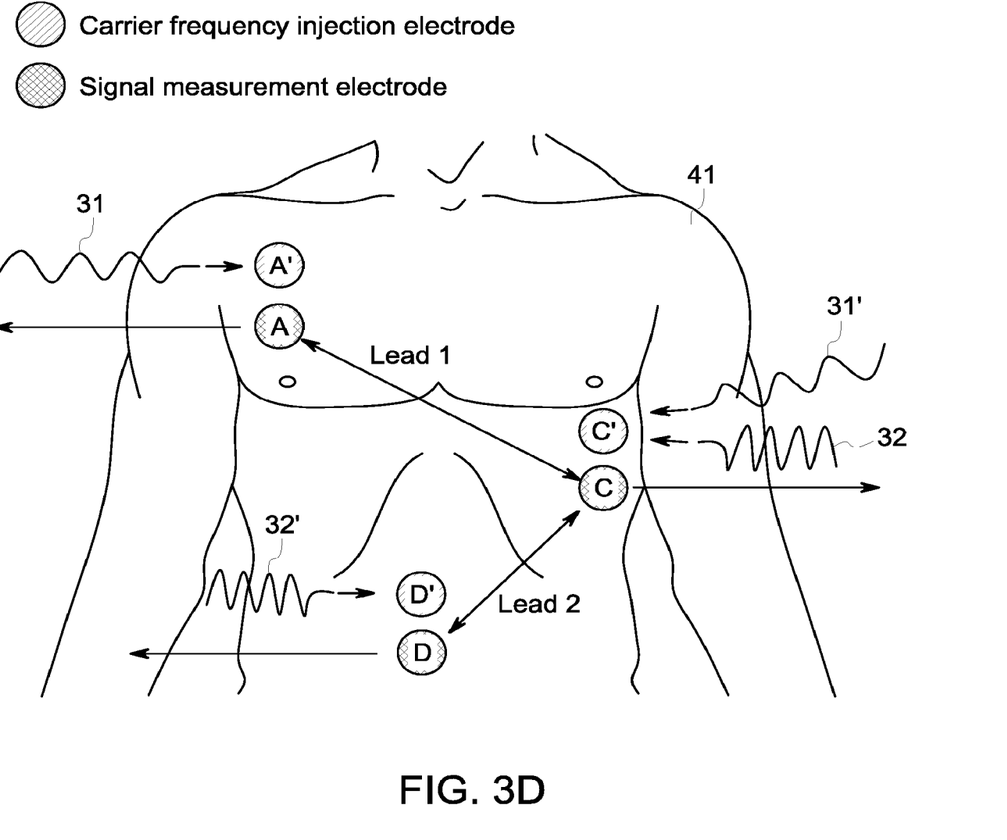
Figure 4:
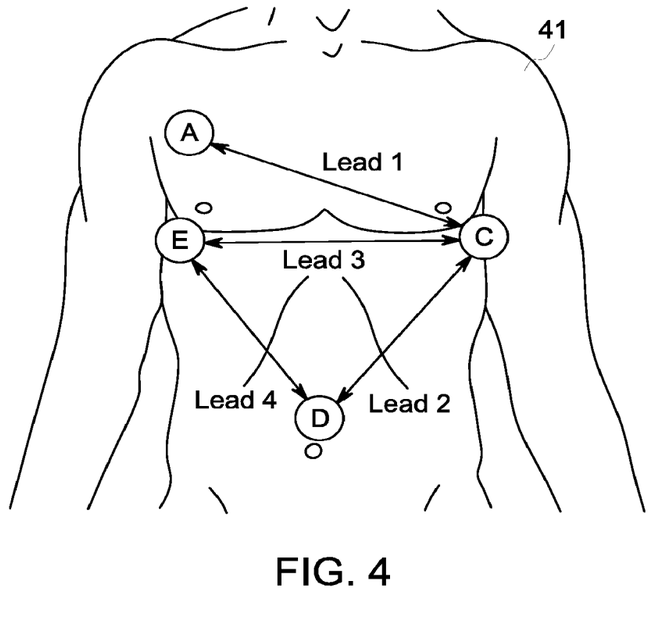
FIG. 4 depicts an exemplary lead arrangement employing four electrodes yielding four leads, including two leads measuring thoracic breath activity and two leads measuring abdominal breath activity.

FIGS. 3A-3D depict a two lead arrangement utilizing only three electrodes. Specifically, the inventors discovered based on their research that one beneficial electrode arrangement for two lead respiration monitoring can be formed by three electrodes positioned in the depicted arrangement. Specifically, electrode A is positioned on the right upper thoracic area, electrode C is positioned on the left lower thoracic area, and electrode D is positioned at the center of the abdomen. One of the three electrodes is a shared electrode between the two respiration leads 1, 2. FIGS. 3A and 3B depict embodiments where the shared electrode is one of the electrodes A and C positioned on the patient's chest. FIG. 3C depicts a third embodiment, where the shared electrode is the abdominal electrode. For certain applications, this lead arrangement may be less desirable because the abdominal breath activity will be reflected in both leads.

Similar to the electrode arrangement depicted and described at FIGS. 2A-2C, signal separation for the three lead arrangement may be provided by either frequency domain separation or time domain separation. FIG. 3A depicts an example employing two different carrier frequencies 31 and 32. Both carrier frequencies are injected simultaneously at electrode C, and both carrier frequencies are sensed at electrode C. Notably, this leads to increased current through electrode C, which increases the sensitivity to the area underneath the common electrode. Thus, additional signal processing may be necessary to filter and deemphasize the contribution of electrode C. This may also provide additional reason to select the common electrode to be a more neutral location where less local contributing activity, such as tissue deformation, is occurring (e.g., one of the chest electrodes rather than the abdominal electrode). Accordingly, electrodes A, B, or C may provide better common electrodes than electrode D.

FIG. 3D depicts the same electrode and lead arrangement as that of FIG. 3A, except that the single-ended sampling method is utilized comprising separate injection and measurement electrodes. Accordingly, injection electrode C' injections both the first and second frequencies 31, 32 (which may be at various phase arrangements as described above). Likewise, measurement electrode C receives the first and second carrier frequencies 31, 32 injected by injection electrodes A' and D', and the respective frequencies are separated therefrom to generate lead 1 and lead 2.

FIG. 4 depicts a four lead arrangement generated using four electrodes. Notably, electrode C is shared by three separate leads. Lead separation may be provided, as described above, by utilization of four different carrier frequencies, or by time division multiplexing.

Figure 5:
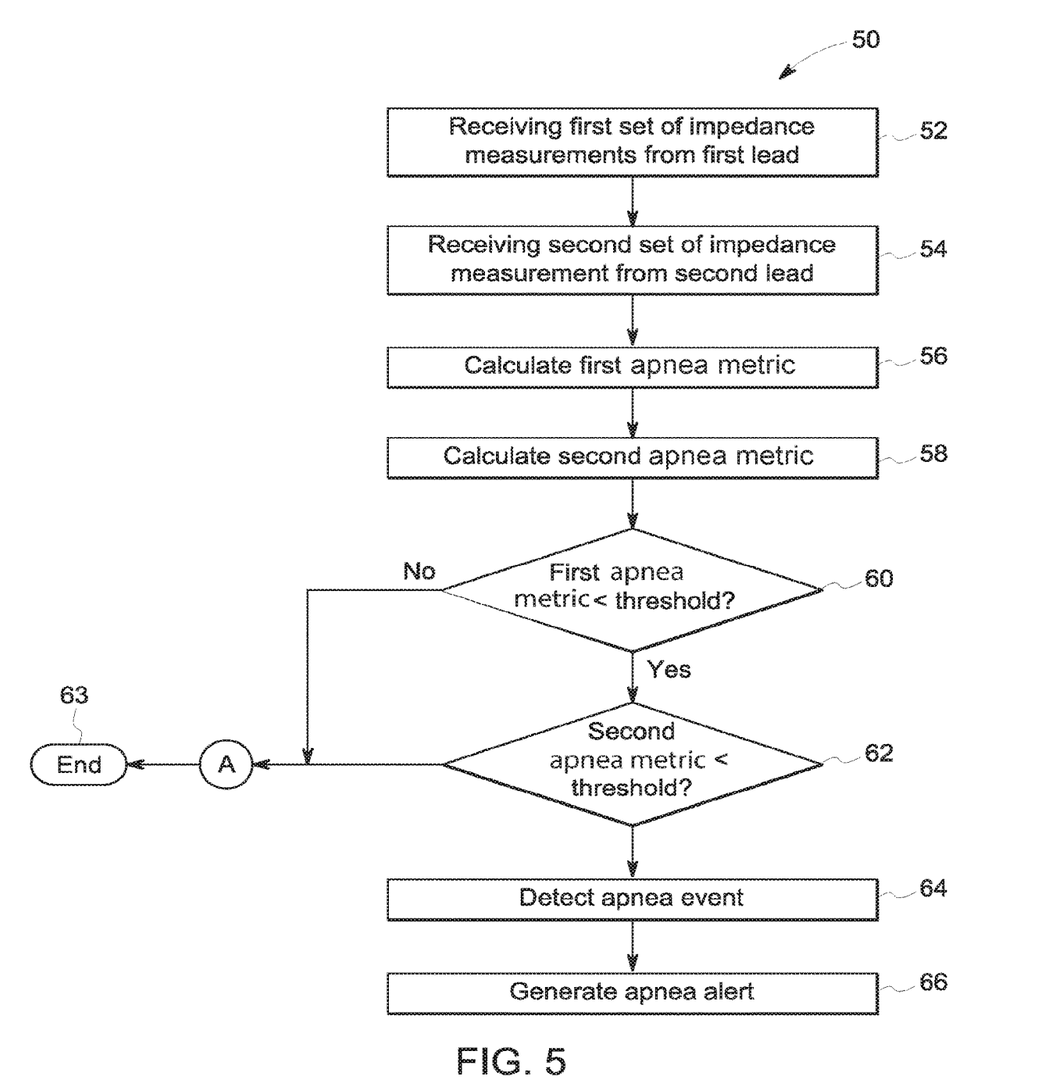
FIGS. 5-6 depict embodiments of methods, or portions thereof, of impedance-based respiration monitoring for apnea detection.
Figure 6:
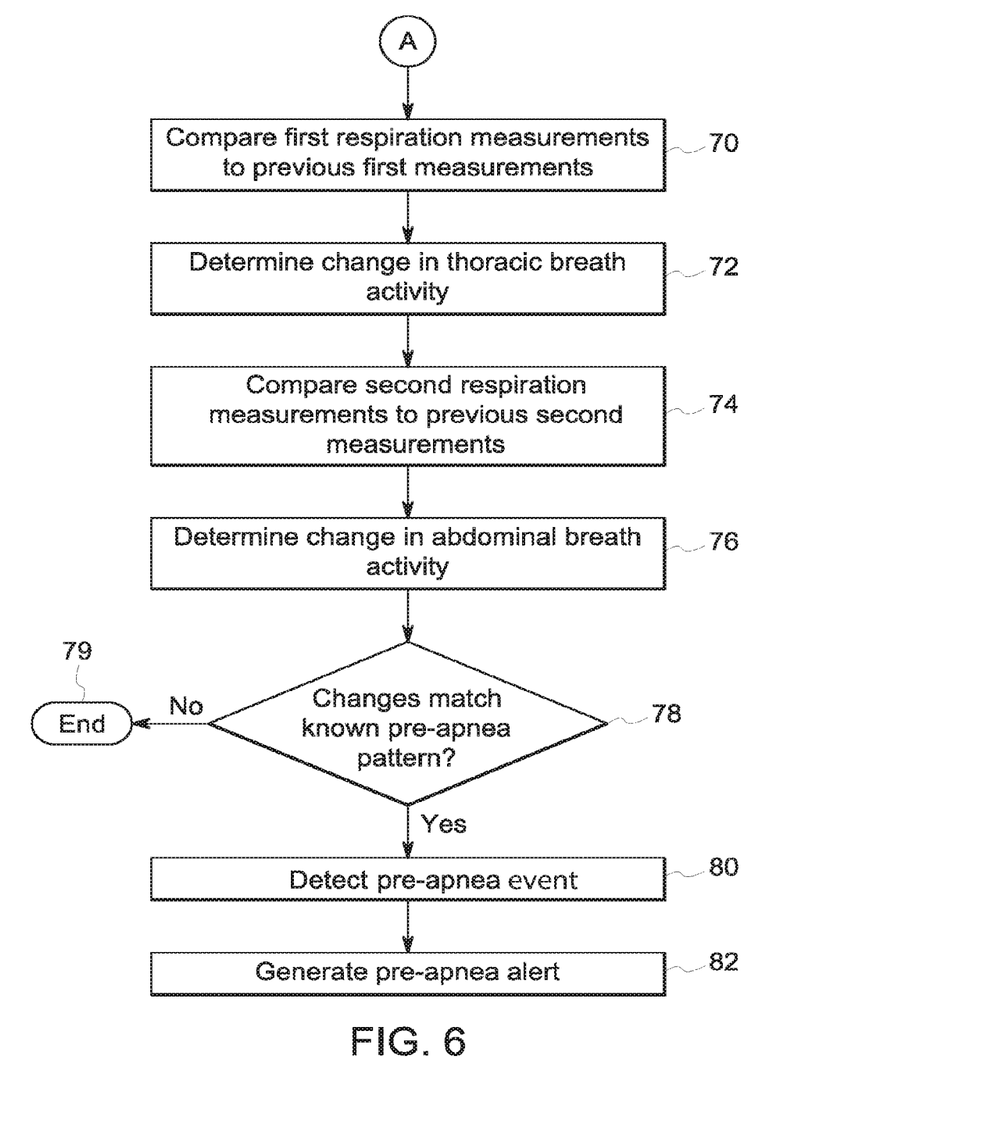

FIGS. 5 and 6 depict embodiments of methods 50, or portions thereof, of impedance-based apnea detection monitoring. The flow charts of FIGS. 5 and 6 represent steps that may be executed, for example, by executing the software instructions of the apnea detection module 17. In the flow chart at FIG. 5, a first series of impedance measurements is received from a first lead at step 52. For example, the series of impedance measurements may represent a period of time, such as a breath cycle or multiple breath cycles of the patient. A second series of impedance measurements from a second lead is received at step 54. As discussed above, the first series of impedance measurements may capture the thoracic breath activity, while the second series of impedance measurements may capture the patient's abdominal breath activity. A first apnea metric is calculated at step 56 based on the first series of impedance measurements. A second apnea metric is calculated at step 58 based on the second series of impedance measurements. For example, the apnea metric may be formed by measuring the amplitude of the signal in a given time window, or measuring the time that the amplitude of the signal has been below a given amplitude threshold. The first and second apnea metrics are then analyzed to determine whether an apnea event has occurred. In certain embodiments, the two apnea metrics may be combined by a mathematical operation to form a single combined apnea metric representing both the first and second apnea metrics, which could be, for example, and average of the first and second apnea metrics.

In the depicted embodiment, the first apnea metric is compared to a first threshold at step 60. Namely, if the first apnea metric is less than the first threshold, then it is determined that insufficient breath activity is represented in the first series of impedance measurements. For example, the first threshold may be a apnea metric of 0, or some other very low respiration activity value that, depending on the period of time represented by the series of impedance measurements, is insufficient for supporting healthy respiration. Alternatively or additionally, the threshold may include an amplitude threshold requiring that the impedance measurements fluctuate by at least a predetermined threshold amount representing indication of continued breath volume. If at step 60 the first apnea metric exceeds the first threshold, then it is determined that respiration is occurring and no apnea event is present. Thus, the inquiry can be ended at step 63. However, if the first apnea metric is less than the first threshold, then step 62 is executed to determine whether the second apnea metric is less than a second threshold. Namely, if the first apnea metric indicates insufficient thoracic breath activity, then the abdominal lead is checked to see if breath activity is occurring there. If the second apnea metric exceeds the second threshold at step 62, then sufficient abdominal breath activity is detected and the inquiry can be ended at step 63. If the apnea metric at step 62 is also insufficient, then an apnea event is detected at step 64.

In various embodiments, the threshold for the second apnea metric may be the same as the threshold for the first apnea metric. Alternatively, the threshold values may be different. For example, the threshold values may be calibrated depending on the patient condition and the intended purpose of the apnea monitoring. For instance, the threshold values may be calibrated based on subsequent analysis activity by the apnea detection module 17, such as pre-apnea pattern analysis exemplified at FIG. 6. In still other embodiments, the first and second apnea metrics may be combined, such as an average, and then compared with a threshold value.

In certain embodiments, additional apnea metrics may be calculated and assessed based on the number of leads. For example in an embodiment with a third respiration lead 3 providing a third series of impedance measurements, a third apnea metric may be calculated, and then compared to a third threshold to determine whether sufficient breath activity is detected in the third lead.

If an apnea event is detected at step 64, then an apnea alert is generated at step 66. For example, the apnea alert may be generated at the user interface 20 of the respiration monitor 5, such as an auditory alert and/or visual alert provided on the display 24. Alternatively or additionally, an alert may be generated at a central monitoring station for the health care unit housing the patient, or may be sent directly to one or more clinician's caring for the patient, such as to a personal electronic device associated with the clinician. The apnea event information may also be stored in memory, such as in the storage system 15 of the apnea monitor 5. Alternatively or additionally, the apnea event information may be transmitted to the computing system of a healthcare facility, such as via wireless network transmission, for further processing and/or storage in the patient's medical record.

The flow chart at FIG. 6 represents logic that may be executed, such as by the apnea detection module 17, to determine whether a change in thoracic and/or abdominal breath activity has occurred that could indicate a pre-apnea event. Such logic may be executed, for example, following the threshold comparison of the first and second apnea metrics to assess whether the impedance measurements are consistent with a known pre-apnea pattern. For example, even though respiration may be present in one or both of the respiration leads 1, 2, changes in the breathing pattern between the upper thoracic area and the abdomen area may indicate, or be consistent with, an upcoming apnea event or another respiratory dysfunction. Thus, further logic may be executed to check for such patterns.

In the example, the first respiration measurements are compared to previous first respiration measurements at step 70. For example, the frequency and/or amplitudes of the current respiration waveforms may be compared to those of previous lead measured respiration waveforms to measure a change in thoracic breath activity at step 72. Similarly, the second respiration measurements are compared to previous second measurements at step 74 to determine a change in abdominal breath activity at step 76. The changes in thoracic and abdominal breath activity are then compared to known pre-apnea patterns at step 78. Similarly, the patterns may be analyzed for indication of any of various respiratory dysfunctions. If no respiratory dysfunction pattern is detected, then the analysis can be ended at step 79. However, if a pre-apnea pattern (or other respiratory dysfunction pattern) match is identified, then an apnea event is detected at step 80 and a corresponding alert is generated at step 82. For example, if a pre-apnea pattern is detected, then a pre-apnea alert is generated at step 82 to alert a clinician of the pre-apnea event. Likewise, information related to the pre-apnea event may be stored in the patient monitor 5 and/or in the patient's medical record.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An impedance-based respiration monitoring system, comprising:
   at least three surface electrodes configured to record impedance respiration data from a patient's torso;
   a signal processing system configured to:
      generate a first respiration lead formed by a first set of surface electrodes from the at least three surface electrodes, the first respiration lead providing a first series of impedance measurements; and
      generate at least a second respiration lead formed by a second set of surface electrodes from the at least three surface electrodes attached to the patient's torso, the second lead providing a second series of impedance measurements;
   wherein the first series of impedance measurements is generated by injecting and detecting a first carrier frequency in the first set of electrodes, and the second series of impedance measurements is generated by injecting and detecting a second carrier frequency in the second set of electrodes;
   wherein the first series of impedance measurements from the first respiration lead measures thoracic breath activity, and wherein the second series of impedance measurements from the second respiration lead measures abdominal breath activity;
   wherein the first set of electrodes includes a first electrode and a second electrode, and the second set of electrodes includes the second electrode and a third electrode, and wherein the system is configured to:
      inject the first carrier frequency at a first phase into the first electrode, and receive the first carrier frequency at the first phase at the second electrode;
      inject the first carrier frequency at a second phase into the second electrode, and receive the first carrier frequency at the second phase at the first electrode;

inject the second carrier frequency at a first phase into the second electrode, and receive the second carrier frequency at the first phase at the third electrode;

inject the second carrier frequency at a second phase into the third electrode, and receive the second carrier frequency at the second phase at the second electrode;

determine the first series of impedance measurements based on the first carrier frequency received at the first and second electrodes;

determine the second series of impedance measurements based on the second carrier frequency received at the second and third electrodes;

a respiration detection module executable on a processor to:

calculate a first respiration metric based on the first series of impedance measurements;

calculate a second respiration metric based on the second series of impedance measurements; and detect a respiration event only when the first respiration metric indicates insufficient breath activity occurring at the patient's chest and the second respiration metric indicates insufficient breath activity occurring at the patient's abdomen.

2. The system of claim 1, wherein the first and second electrodes are positioned on the patient's chest, and the third electrode is positioned on the patient's abdomen.

3. The system of claim 1, wherein the first set of electrodes and the second set of electrodes comprise a four electrode arrangement, wherein the first set of electrodes includes a first electrode and a second electrode positioned on the patient's chest, and the second set of electrodes includes a third electrode and a fourth electrode, wherein at least one of the third and fourth electrodes is positioned on the patient's abdomen.

4. The system of claim 1, wherein the first series of impedance measurements and the second series of impedance measurements are generated by injecting and detecting a carrier frequency in the first set of electrodes and the second set of electrodes, respectively, utilizing time division multiplexing to differentiate between the first series of impedance measurements in the first respiration lead and the second series of impedance measurements in the second respiration lead.

5. A method of impedance-based respiration metric monitoring using a first set of electrodes and a second set of electrodes comprising a three electrode arrangement, wherein the first set of electrodes includes a first electrode and a second electrode, and the second set of electrodes includes the second electrode and a third electrode, the method comprising:

injecting a first carrier frequency at a first phase into the first electrode, and receiving the first carrier frequency at the first phase at the second electrode;

injecting the first carrier frequency at a second phase into the second electrode, and receiving the first carrier frequency at the second phase at the first electrode;

injecting a second carrier frequency at a first phase into the second electrode, and receiving the second carrier frequency at the first phase at the third electrode;

injecting the second carrier frequency at a second phase into the third electrode, and receiving the second carrier frequency at the second phase at the second electrode;

determining a first series of impedance measurements based on the first carrier frequency received at the first and second electrodes, wherein the first series of impedance measurements measures thoracic breath activity;

determining a second series of impedance measurements based on the second carrier frequency received at the second and third electrodes, wherein the second series of impedance measurements measures abdominal breath activity;

calculating a first respiration metric based on the first series of impedance measurements;

calculating a second respiration metric based on the second series of impedance measurements; and detecting a respiration event only when both the first respiration metric indicates insufficient breath activity occurring at the patient's chest and the second respiration metric indicates insufficient breath activity occurring at the patient's abdomen.

6. The method of claim 5, wherein the first and second electrodes are positioned on the patient's chest and the third electrode is positioned on the patient's abdomen.

7. The method of claim 5, wherein the first set of electrodes and the second set of electrodes comprise a four electrode arrangement, wherein the first set of electrodes includes a first electrode and a second electrode positioned on the patient's chest, and the second set of electrodes includes a third electrode and a fourth electrode, wherein at least one of the third and fourth electrodes is positioned on the patient's abdomen.

8. The method of claim 5, further comprising comparing the first respiration metric to a first threshold and determining whether the first respiration metric indicates insufficient breath activity based on the comparison; and based on the first respiration metric indicating insufficient breath activity, comparing the second respiration metric to a second threshold to determine whether the second respiration metric indicates insufficient breath activity.

9. The method of claim 8, wherein the second threshold is dependent on the comparison of the first respiration metric to the first threshold.

* * * * *